US012606821B2

(12) United States Patent
Yang et al.

(10) Patent No.: US 12,606,821 B2
(45) Date of Patent: Apr. 21, 2026

(54) METHOD FOR CONSTRUCTING LIBRARY ON BASIS OF RNA SAMPLES, AND USE THEREOF

(71) Applicant: BGI SHENZHEN, Shenzhen (CN)

(72) Inventors: Xi Yang, Shenzhen (CN); Yanru Xing, Shenzhen (CN); Wenjing Wang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 1158 days.

(21) Appl. No.: 17/555,494

(22) Filed: Dec. 19, 2021

(65) Prior Publication Data

US 2022/0186212 A1     Jun. 16, 2022

Related U.S. Application Data

(63) Continuation of application No. PCT/CN2019/091993, filed on Jun. 20, 2019.

(51) Int. Cl.
| | |
|---|---|
| *C12N 15/10* | (2006.01) |
| *C12Q 1/6806* | (2018.01) |
| *C12Q 1/6855* | (2018.01) |
| *C12Q 1/6876* | (2018.01) |

(52) U.S. Cl.
CPC ....... *C12N 15/1096* (2013.01); *C12Q 1/6806* (2013.01); *C12Q 1/6855* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 12,442,045 | B2 * | 10/2025 | Williams .............. | C12Q 1/6886 |
| 2016/0076094 | A1 | 3/2016 | Thielen et al. | |
| 2017/0101674 | A1 * | 4/2017 | So ........................ | C12Q 1/6806 |
| 2018/0230527 | A1 * | 8/2018 | Fang .................... | C12Q 1/6869 |

FOREIGN PATENT DOCUMENTS

| | | |
|---|---|---|
| CN | 102534813 A | 7/2012 |
| CN | 105143525 A | 12/2015 |
| CN | 105985945 A | 10/2016 |
| CN | 105985949 A | 10/2016 |
| CN | 106801050 A | 6/2017 |
| CN | 107849561 A | 3/2018 |
| WO | 0245472 A2 | 6/2002 |
| WO | 2017182578 A1 | 10/2017 |
| WO | WO-2018053365 A1 * | 3/2018 .......... C12Q 1/6853 |
| WO | 2018149091 A1 | 8/2018 |
| WO | 2018193233 A1 | 10/2018 |

OTHER PUBLICATIONS

Thermo Scientific (10X DNA Ligase Buffer) (Year: 2012).*
Library Preparation and Multiplex Capture for Massive Parallel Sequencing Applications Made Efficient and Easy, PLOS one, 7, 11, e48616 (Year: 2012).*
Mao, S., et. al., Identification of artifactual microarray probe signals constantly present in multiple sample types, BioTechniques, Aug. 2012, pp. 91-98, vol. 53, No. 2, DOI 10.2144/0000113903, published by Future Science Group, London GB.
English translation of Chinese 1st Office Action & 1st Search, CN Application No. CN201980097411.8, dated May 30, 2023, entire document.
The extended European search report in European Patent Application No. 19934021.7, dated Aug. 29, 2022.

* cited by examiner

*Primary Examiner* — Juliet C Switzer
*Assistant Examiner* — Brian Ellis Young
(74) *Attorney, Agent, or Firm* — BOND, SCHOENECK & KING, PLLC; George R. McGuire

(57)     ABSTRACT

Provided are a method for constructing a library based on an RNA sample and uses thereof. The method includes: step 1 of subjecting the RNA sample to a reverse transcription reaction to obtain DNA-RNA hybrid strands; step 2 of performing reaction of the DNA-RNA hybrid strands with an endoribonuclease, a first DNA polymerase, a second DNA polymerase, and dATPs to obtain a double-stranded DNA added with dA-tail, where the first DNA polymerase has a 5'-3' exonuclease activity and a 3'-5' exonuclease activity, and the second DNA polymerase has no 3'-5' exonuclease activity; step 3 of ligating the double-stranded DNA added with dA-tail and a sequencing adaptor to obtain a ligated product; and step 4 of subjecting the ligated product to PCR amplification to obtain a sequencing library.

12 Claims, 3 Drawing Sheets

Specification includes a Sequence Listing.

METHOD FOR CONSTRUCTING LIBRARY ON BASIS OF RNA SAMPLES, AND USE THEREOF

CROSS-REFERENCE TO RELATED APPLICATION

This application is a continuation of International Application No. PCT/CN2019/091993, filed on Jun. 20, 2019, which is incorporated herein by reference in its entirety.

FIELD

The present disclosure relates to the field of gene sequencing, and in particular to a method for constructing a library based on RNA samples, and use thereof.

BACKGROUND

The conventional Total RNA-Seq is a process that based on an RNA sample, reverse transcriptase is used for a first strand synthesis, then a classic RNase H-DNA polymerase I scheme is used for a second strand synthesis, and then the adaptors are ligated. It is the general scheme of respective major library construction reagent companies, and the scheme of double-stranded cDNA synthesis has a history of 20 to 30 years. In another alternative scheme, the SMATRer technology is adopted, i.e., the adaptors are ligated by utilizing the template-switch activity of reverse transcriptase during reverse transcription, and such a technology has a high speed in term of library construction, but requires specific and expensive reverse transcriptase (e.g., Super-Script II).

The library construction and sequencing methods of RNA samples need to be further improved.

SUMMARY

The present disclosure aims to solve at least one of the technical problems in the related art. In this regard, an object of the present disclosure is to provide a method for constructing a library based on an RNA sample, a kit, and uses thereof.

Applicant has discovered through a long-term research that a main process of the conventional RNA-based library construction and sequencing method includes: removing ribosomal RNAs (rRNAs) from RNAs, then synthesizing a double-stranded cDNA, purifying the double-stranded cDNA, performing end repair/dA-tail addition, ligating adaptors, purifying the ligated product, selecting fragments, and finally performing library amplification. In this conventional method, it is required to purify the synthesized double-stranded cDNA prior to the end repair and dA-tail addition. Among them, the steps of synthesis of double-stranded cDNA, purification, end repair and dA-tail addition are independent from one another, such that this library construction method is relatively slow and will take a long period of time, and due to multiple steps of purification, the material and labor costs thereof is relatively high when used for production in a production line. Additionally, due to the multiple steps of purification steps, a risk of failure will be very high if the operation is improper.

DNA-RNA hybrid strands can be formed through the first strand synthesis of cDNA, and the second strand synthesis is performed by using the DNA-RNA hybrid strands, RNase H, and DNA polymerase I. According to the principle of the second strand synthesis, the RNA strand is digested by RNase H to produce nicks and to provide corresponding primers for DNA polymerase I. DNA polymerase I has three kinds of activity, i.e., a DNA polymerase activity, a 3'-5' exonuclease activity, and a 5'-3' exonuclease activity. Therefore, the DNA polymerase I can use the RNase H-digested fragments as primers and use the first strand cDNA as a template for synthesis. In the process of synthesis, with the 5'-3' exonuclease activity, the RNA fragments can be removed from the hybrid strand and replaced with the second strand cDNA. The 3'-5' exonuclease activity guarantees the accuracy of the synthesis, and blunts the ends after the synthesis is completed. Therefore, the product formed through the second strand synthesis basically has blunted ends. However, DNA polymerase I has a main shortcoming, i.e., side reactions may occur when reacting at a temperature of 20° C. or higher, which may result in the formation of neck loop structures and the defect of the 3'-end, thereby reducing the synthesis efficiency. Therefore, it is necessary to remove DNA polymerase I after the second strand synthesis is completed. In addition, E. coli DNA ligase is usually used in the synthesis process of the second strand to repair the nicks during the second strand synthesis. However, the use of expensive E. coli DNA ligase significantly increases the cost of RNA library construction, which is obviously unfavorable for the determination of a large amount of samples.

Applicant found through researches that during the process of second strand synthesis, it is unnecessary to repair the nicks caused by the side reactions of DNA polymerase I with E. coli DNA ligase, because these nicks can be repaired in the subsequent ligation step; and RNA-Seq is different from cDNA cloning and involves small fragments, and DNA polymerase can complete the synthesis of the entire second strand. In addition, in strand-splitting RNA-Seq, the second strand is a strand to be removed, and its integrity is of little importance.

To this end, the present disclosure provides a method for constructing a library based on an RNA sample, which avoids the use of E. coli DNA ligase, thereby saving costs and ensuring the stability of the reaction system. Besides, in the process of second strand synthesis, DNA polymerase is directly used to add dA-tail, thereby combining second strand synthesis with end repair and dA-tail addition together, saving a lot of time and saving the reagents consumed by stepwise procedures.

Specifically, the present disclosure provides the following technical solutions.

According to a first aspect of the present disclosure, the present disclosure provides a method for constructing a library based on an RNA sample. The method includes: step (1) of subjecting the RNA sample to a reverse transcription reaction to obtain DNA-RNA hybrid strands; step (2) of performing reaction of the DNA-RNA hybrid strands with an endoribonuclease, the first DNA polymerase, the second DNA polymerase, and dATPs to obtain a double-stranded DNA added with dA-tail, where the first DNA polymerase has a 5'-3' exonuclease activity and a 3'-5' exonuclease activity, and the second DNA polymerase has no 3'-5' exonuclease activity; step (3) of ligating the double-stranded DNA added with dA-tail and a sequencing adaptor to obtain a ligated product; and step (4) of subjecting the ligated product to PCR amplification to obtain a sequencing library.

The present solution integrates the second strand synthesis with end repair and dA-tail addition. The most time-consuming second strand synthesis is combined with the processes of purification, and end repair/dA-tail addition, thereby reducing the consumption of reagents (purification magnetic beads and end repair/dA-tail addition reagents are omitted), and saving a lot of time (for large-scale automated production, each purification shall be performed overnight and the conventional procedure requires at least 3 days, while the current procedure requires 2 days; time for manual library construction is reduced from about 10 hours to about 7 hours, saving ⅓ of the time; the above timekeeping starts from the total RNA of mammalian cells to the completion of PCR purification). Moreover, by avoiding the use of *E. coli* DNA ligase, the costs can be reduced (the expensive *E. coli* DNA ligase is no longer needed), and the stability of the buffer can be ensured (the cofactor NAD of *E. coli* DNA ligase is likely to be degraded).

According to an embodiment of the present disclosure, the above-mentioned method for constructing a library based on an RNA sample may further include the following technical features.

In some embodiments of the present disclosure, the endoribonuclease is RNase H. As one kind of endoribonuclease, RNase H can hydrolyze the phosphodiester bond of RNA strand hybridized to the DNA strand, that is, RNase H can decompose the RNA strand in the DNA-RNA hybrid strands.

In some embodiments of the present disclosure, the first DNA polymerase is DNA polymerase I; and the second DNA polymerase is selected from the group consisting of Taq DNA polymerase, Tth DNA polymerase, Bst DNA polymerase, Bst DNA polymerase of larger fragment, Klenow Fragment (exo-), and combinations thereof. As an example, the Taq DNA polymerase allows a reaction at a higher temperature to add the dA-tailing to the end of the DNA strand, and DNA polymerase I can be inactivated through treatment at a relatively high temperature to prevent subsequent side reactions; and the 3'-end defect generated during re-heating can be repaired by Taq DNA polymerase. Tth DNA polymerase, similar to Taq DNA polymerase, is a thermostable enzyme with a molecular weight of about 94 kDa, and has no 3'-5' DNA exonuclease activity and has similar functions as Taq DNA polymerase.

In some embodiments of the present disclosure, the reaction in step 2 includes: reacting at 10° C. to 20° C. for at least 1 hour and then reacting at 70° C. to 80° C. for 10 to 30 minutes to obtain the double strand DNA added with A-tailing. In this way, the repaired double-stranded DNA added with dA-tail can be directly obtained in the same reaction system.

In some embodiments of the present disclosure, a buffer used in the reaction in step 2 includes magnesium ions at a final concentration of 5 mM to 40 mM, Tris-Cl having a pH value between 6.5 and 8.5, and sodium or potassium ions at a final concentration of less than 100 mM. The buffer has relatively low ion concentration, and easy to obtain and inexpensive.

In some embodiments of the present disclosure, a buffer used to perform the reaction in step 2 is a T4 DNA ligase buffer, a T4 polynucleotide kinase buffer, NEBuffer™ 2, or NEBuffer™ 4. These buffers have low ion concentrations, are very common and very cheap.

In some embodiments of the present disclosure, step 1 further includes: step 1-1 of mixing and treating the RNA sample with a reverse transcription buffer and 5' end-phosphorylated random primers at 80° C. to 95° C. for 5 minutes to obtain a fragmented RNA product; and step 1-2 of mixing the fragmented RNA product with dNTPs, actinomycin D, an RNase inhibitor and reverse transcriptase for the reverse transcription reaction to obtain a first strand cDNA product.

In some embodiments of the present disclosure, the reverse transcription reaction includes 10 minutes to 15 minutes at 25° C. to 30° C., 10 minutes to 20 minutes at 45° C. to 55° C., and 10 minutes to 20 minutes at 70° C. to 75° C.

In some embodiments of the present disclosure, the random primers have a length of 6 to 8 random nucleotides. Through the treatment with phosphorylated random primers, it can be ensured that the 5'-end of the first strand is phosphorylated and can be directly ligated, for example, without requiring a subsequent treatment with T4 polynucleotide kinase prior to the ligation with the adaptors.

In some embodiments of the present disclosure, prior to step 4, the method further includes: purifying the ligated product using magnetic beads.

In some embodiments of the present disclosure, the RNA sample is a total RNA sample, an oligo (dT)-enriched mRNA sample, or an rRNA-free RNA sample.

According to a second aspect of the present disclosure, the present disclosure provides a sequencing library constructed with the method described in any embodiment of the first aspect of the present disclosure.

According to a third aspect of the present disclosure, the present disclosure provides a method for sequencing an RNA sample, including: constructing a sequencing library based on an RNA sample with the method described in any embodiment of the first aspect of the present disclosure; and sequencing the sequencing library to obtain sequencing information of the RNA sample.

According to a fourth aspect of the present disclosure, the present disclosure provides a kit including: RNase H; DNA polymerase I; and any one of Taq DNA polymerase, Tth DNA polymerase, Bst DNA polymerase, Bst DNA polymerase of larger fragment, or Klenow Fragment (exo-).

According to the embodiments of the present disclosure, the above-mentioned kit may further include the following technical features.

In some embodiments of the present disclosure, the kit further includes random primers, where the random primers are 5' end-phosphorylated and have a length of 6 to 8 random nucleotides.

In some embodiments of the present disclosure, the kit further includes at least one of dNTP, actinomycin D, an RNase inhibitor, a reverse transcriptase, a T4 DNA ligation buffer, a T4 polynucleotide kinase buffer, NEBuffer™ 2 or NEBuffer™ 4, magnesium ions, Tris-Cl, sodium ions or potassium ion, or universal sequencing adaptors. As an example, NEBuffer™ 4 is a relatively complete buffer system available on the market, and is adapted to a variety of enzymes to ensure the progress of the enzymatic reaction; NEBuffer™ 2 can also achieve the same purpose. The components contained in the kit can provide conditions and basis for library construction using the RNA sample and sequencing, thereby achieving the successful library construction and sequencing. These components can be independently packaged, or packaged together as needed for convenient use.

BRIEF DESCRIPTION OF DRAWINGS

The above and/or additional aspects and advantages of the present disclosure will become apparent and easy to understand from the description of the embodiments in conjunction with the following drawings, in which.

US 12,606,821 B2

5

Figure 1:
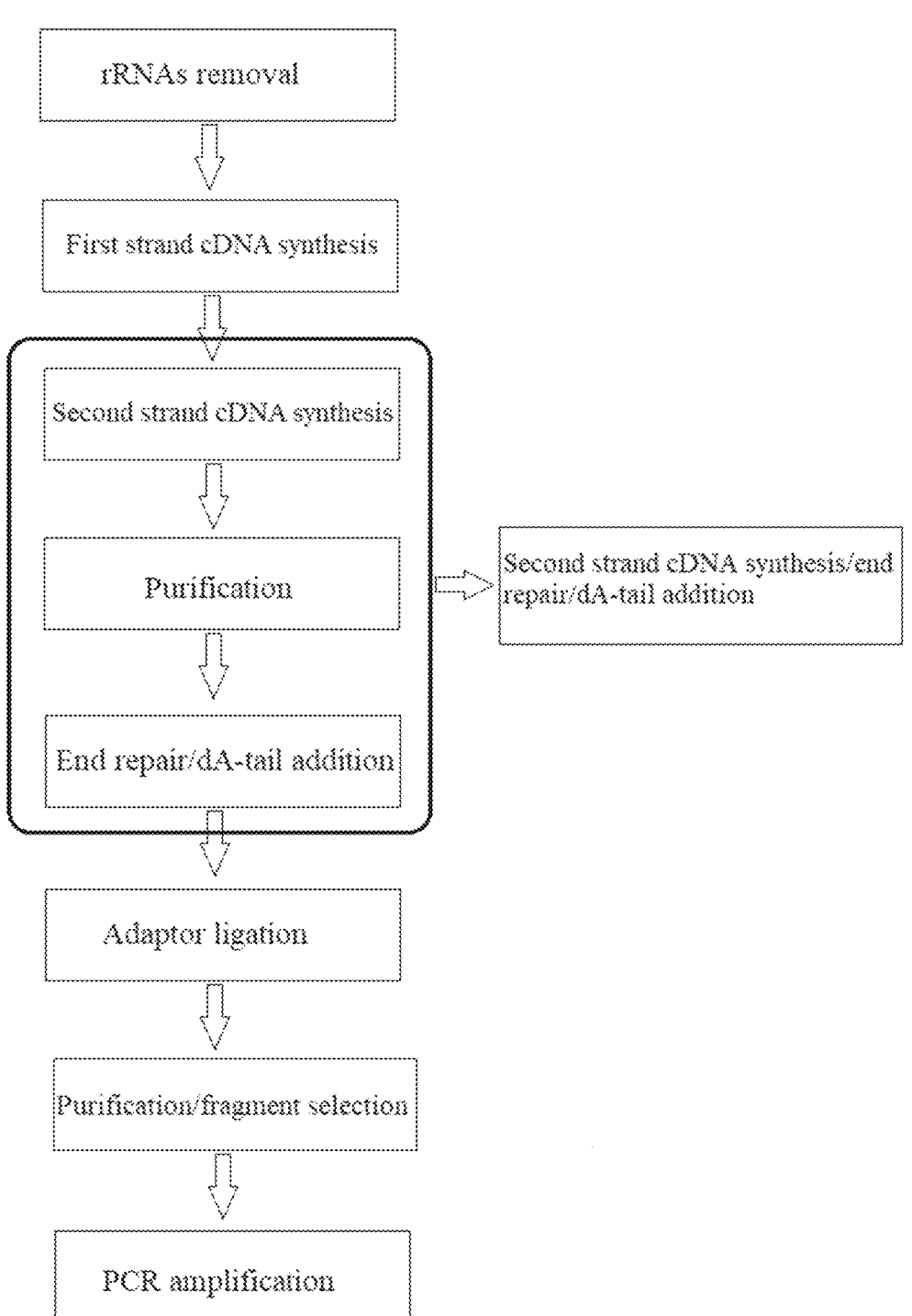
FIG. 1 is a schematic flow chart of a method for constructing a library based on an RNA sample according to an embodiment of the present disclosure.
Figure 2:
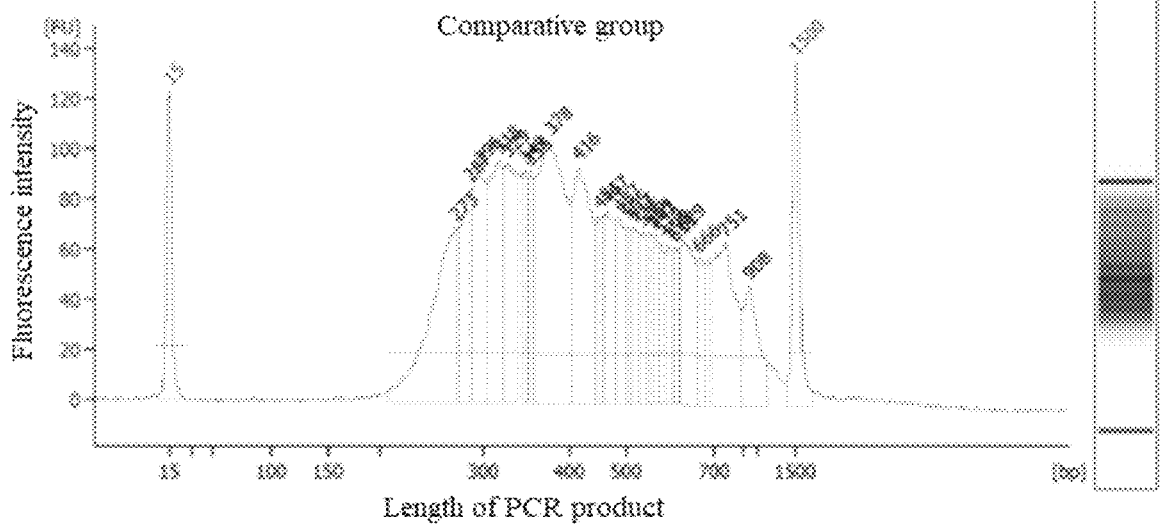
Figure 2:
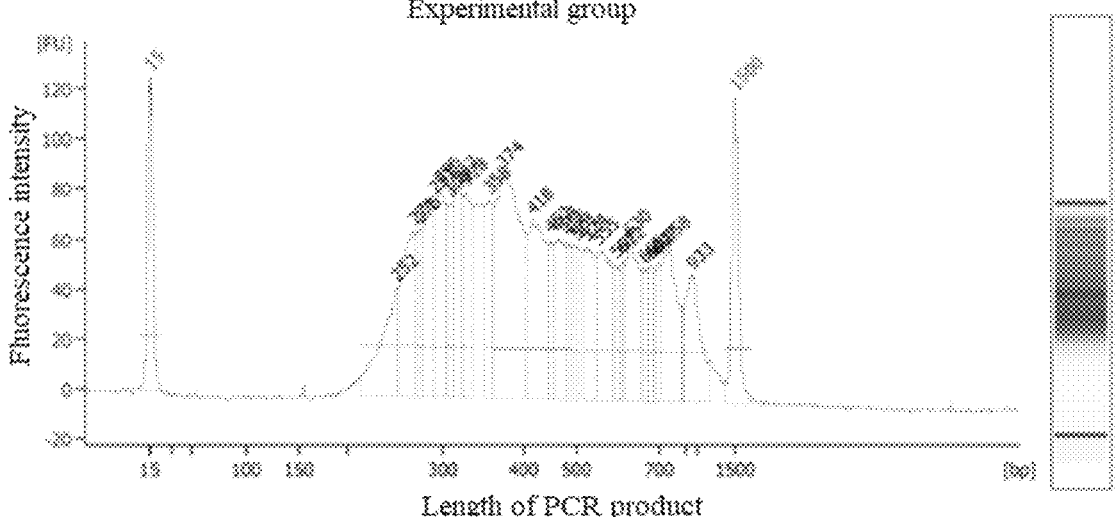

FIG. 2 is a capillary electrophoresis diagram (detected by Agilent 2100 Electrophoresis Bioanalyzer Instrument (hereafter referred as bioanalyzer 2100)) of lengths of PCR products obtained according to different schemes provided by embodiments of the present disclosure.

Figure 3:
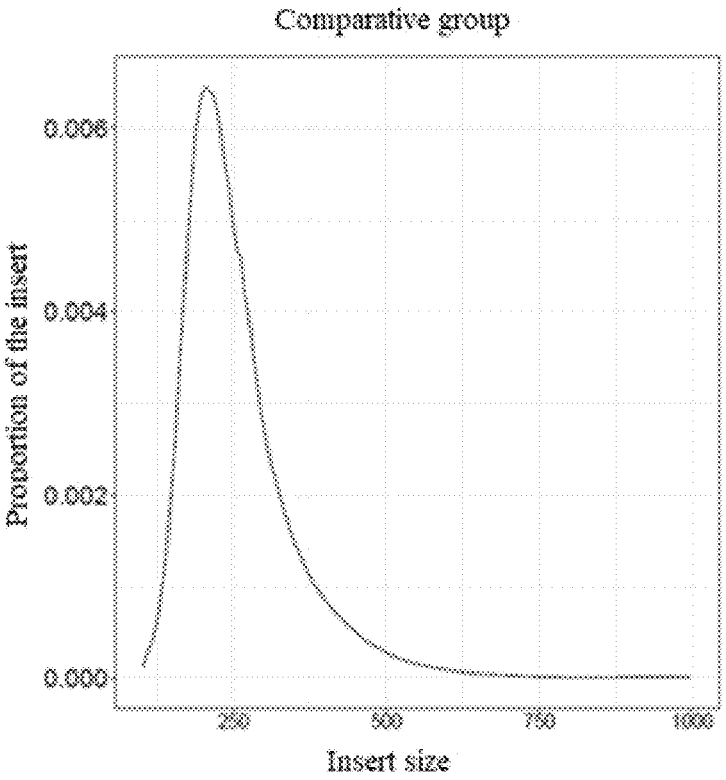
Figure 3:
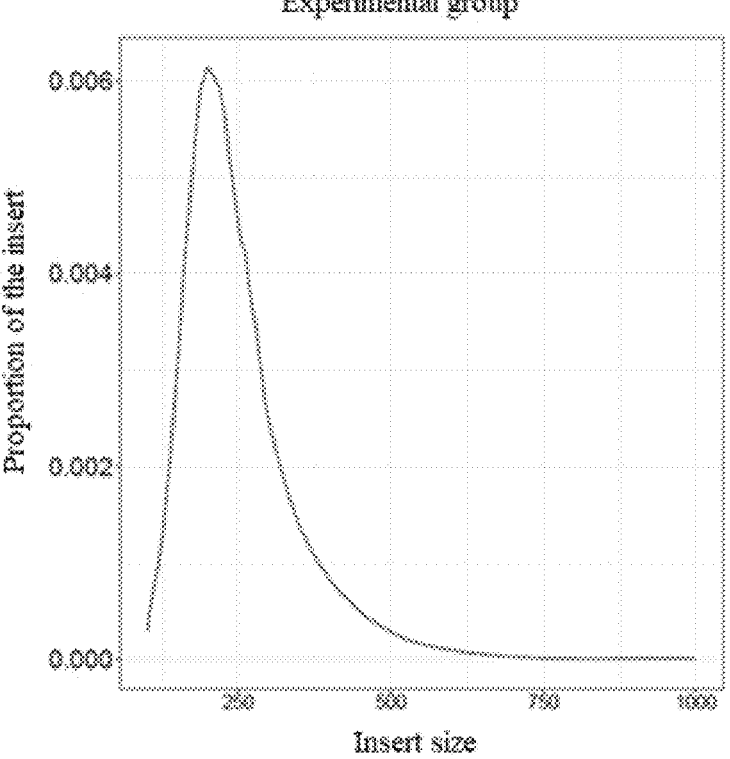

FIG. 3 is a diagram illustrating proportions of insert fragments of different schemes according to embodiments of the present disclosure.

DESCRIPTION OF EMBODIMENTS

The embodiments of the present disclosure are described in detail below. Examples of the embodiments are illustrated in the accompanying drawings, throughout which the same or similar reference numerals indicate the same or similar elements or elements with the same or similar functions. The embodiments described below with reference to the accompanying drawings are exemplary, and are intended to explain the present disclosure, but should not be construed as limiting the present disclosure.

In order to have a more intuitive understanding of the present disclosure, the terms present in the present disclosure are explained and described below. Those skilled in the art shall understand that these explanations and descriptions are only for facilitating the understanding and should not be regarded as limiting the protection scope of the present application.

The present disclosure provides a method for constructing a library based on an RNA sample, which integrates second strand synthesis and end repair, dA-tail addition into one step. For example, by adding Taq DNA polymerase to a system of the second strand synthesis, the DNA polymerase is directly inactivated after the second strand synthesis, while the dA-tailing addition is achieved. This scheme ensures the continuity of the reaction buffer and omits the use of *E. coli* DNA ligase, thereby significantly reducing the cost of library construction and sequencing.

According to one aspect of the present disclosure, the present disclosure provides a method for constructing a library based on an RNA sample. The method includes: step (1) of subjecting the RNA sample to a reverse transcription reaction to obtain DNA-RNA hybrid strands; step (2) of performing reaction of the DNA-RNA hybrid strands with an endoribonuclease, a first DNA polymerase, a second DNA polymerase, and dATPs to obtain a double-stranded DNA added with dA-tail, where the first DNA polymerase has a 5'-3' exonuclease activity and a 3'-5' exonuclease activity, and the second DNA polymerase has no 3'-5' exonuclease activity; step (3) of ligating the double-stranded DNA added with dA-tail and a sequencing adaptor to obtain a ligated product; and step (4) of subjecting the ligated product to PCR amplification to obtain a sequencing library.

In the present disclosure, the term "endoribonuclease" refers to an enzyme that destroys the phosphodiester bond on the RNA strand to form nicks. The endoribonuclease can destroy the phosphodiester bond on single-stranded RNA, and can also destroy the phosphodiester bond on double-stranded RNA or the phosphodiester bond of RNA strand in the DNA-RNA hybrid strands, to form nicks due the destroying, such that the nicks can be utilized for synthesis of a new nucleic acid strand. In at least some embodiments, the endoribonuclease is RNase H. In the process of synthesizing double-stranded cDNA by using the RNase H, nicks can be formed on the RNA strand by controlling the temperature of the reaction, instead of quickly and completely degrading the RNA strand. For example, the temperature of the reaction can be controlled within a range of 10° C. to 20° C., and the RNase H can digest the RNA strand with a very slow speed by using a suitable and relatively low concentration of RNase H. In this way, the RNA strand will not be degraded quickly and completely, and short RNA fragments can be formed. The second strand cDNA can be synthesized by using the short RNA fragments as primers and the DNA strand as a template.

DNA polymerase has a 5'-3' polymerase activity, and thus it can synthesize a new DNA strand using DNA as a template. In addition, the first DNA polymerase further has a 3'-5' exonuclease activity, capable of ensuring the accuracy in the synthesis process. The first DNA polymerase also has a 5'-3' exonuclease activity, capable of completely removing the remaining RNA strands in the first strand cDNA product and replace them with the DNA strand. The final product of the reaction of the first DNA polymerase is end-blunted. The subsequent adaptor ligation uses TA cloning, which requires the end of the product contain a dA-tail. Therefore, the second DNA polymerase is also added during the reaction, and the second DNA polymerase has no 3'-5' exonuclease activity and can add the dA-tail to the end of the DNA strand. Thus, the second strand synthesis, the end repair and dA-tail addition can be completed in the same reaction system in one step by using the first DNA polymerase, the second DNA polymerase and the RNase H, thereby greatly saving the time for library construction. Moreover, multiple steps of purification are avoided, thereby reducing the reagents to be used and lowering the cost of library construction.

In at least some embodiments, the first DNA polymerase may be DNA polymerase I, which has the DNA polymerase activity, the 3'-5' exonuclease activity, and the 5'-3' exonuclease activity. It can be used for synthesis by using the RNase H-digested fragments as primers and the first strand cDNA as a template. In the process of synthesis, the 5'-3' exonuclease activity allows the RNA fragments on the hybrid strands to be removed and replaced with the second strain cDNA. The accuracy of the synthesis is guaranteed by the 3'-5' exonuclease activity.

In at least some embodiments, the second DNA polymerase can be Taq DNA polymerase or Tth DNA polymerase. As an example, Taq DNA polymerase catalyzes the reaction at a relatively higher temperature to add dA-tail to the end of the DNA strand, and the first DNA polymerase can be inactivated to prevent subsequent side reactions; and in the process of heating, the defects generated during the synthesis of the new DNA strand can be repaired by Taq DNA polymerase. On basis of the function of the second DNA polymerase, Klenow Fragment (exo-) can be used to play the role of the second DNA polymerase. Klenow Fragment (exo-) is a mutant of a large fragment of *E. coli* polymerase I which lacks the exonuclease activity and retains the 5'-3' polymerase activity of DNA polymerase I, i.e., the 5'-3' and 3'-5' exonuclease activities of the complete DNA polymerase are missing.

In at least some embodiments, the RNA sample is total RNA. The rRNA shall be removed to obtain the interested mRNA. For example, the digestion treatment with RNase H can be performed at 37° C., so as to completely degrade rRNA into small fragments of 4 to 6 bases.

The solutions of the present disclosure will be explained below in conjunction with examples. Those skilled in the art can understand that the following examples are only for the purpose of illustrating the present disclosure, and should not be regarded as limiting the scope of the present disclosure. Where specific techniques or conditions are not indicated in the examples, the procedures shall be carried out in accordance with the techniques or conditions described in the literatures in the related field or in accordance with the product specification. The reagents or instruments used without indication of the manufacturers are all conventional products that are commercially available.

EXAMPLE

The present example provides different methods for constructing a sequencing library based on an RNA sample and sequencing. The experiments were divided into comparative groups and experimental groups. Two parallel experiments were conducted for the comparative groups, and two parallel experiments were conducted for the experimental groups. The comparative groups adopted the conventional RNA-seq, i.e., including the synthesis of DNA-RNA hybrid strands through reverse transcription based on the RNA sample, the synthesis of double-stranded cDNA using RNase H and DNA polymerase I, purification, end repair and dA-tail addition, adaptor ligation, purification of the ligated product, fragment selection, and finally library amplification and sequencing. The principle of such a solution was consistent with that of NEBNext Ultra II RNA Directed Library Preparation Kit (NEB #E7760).

The experimental groups employed a different reaction system, which integrated the synthesis of double-stranded cDNA, purification, end repair and dA-tail addition together. In the experimental groups, dUTPs were incorporated during the synthesis of the second strand cDNA, such that uracil DNA glycosylase could be used to specifically remove the second strand cDNA and retain the first strand prior to the PCR, thereby ensuring the directionality of the library.

The treatment process of the experimental groups specifically included the following steps.

rRNAs were removed from 500 ng of total RNA of white blood cells by using the RNase H method.

Fragmentation: 4 μL of 5× reverse transcription buffer and 0.5 μL of 100 ng/μL Pi-N6 random primers (5'-NNNNNN-3', with phosphorylated 5'-end, where N represents any one of bases A, T, C or G) were added and mixed, immediately inserted in ice after standing at 85° C. for 5 minutes.

First Strand Synthesis:

Actinomycin D to 0.5 g/L (dilute before use and discard after use). Add following system:

| | Volume |
|---|---|
| 10 mM dNTP | 1.0 μL |
| 0.5 g/L actinomycin D | 1.0 μL |
| 40 U/μL RNase inhibitor | 0.5 μL |
| 200 U/μL reverse transcriptase | 1.0 μL |
| Total | 3.5 μL |

The reverse transcription was performed in a PCR instrument at 25° C. for 10 minutes, at 45° C. for 15 minutes, and at 70° C. for 15 minutes; followed by cooling down to 4° C. and keeping the temperature. The reaction product was taken and inserted in ice.

For the second strand synthesis, the following system was further added:

| | Volume |
|---|---|
| 10X T4 DNA ligase buffer | 5.0 μL |
| 10 mM dUTP | 1.0 μL |

| | Volume |
|---|---|
| 10 mM dATP | 2.0 μL |
| 5 U/μL RNase H | 0.2 μL |
| 10 U/μL DNA polymerase I | 2.5 μL |
| 5 U/μL Taq DNA polymerase | 0.2 μL |
| Nuclease-free water | 19.1 μL |
| Total | 30 μL |

On a PCR instrument, the system reacted at 16° C. for 1 hour (second strand synthesis) and at 70° C. for 15 minutes (for inactivating DNA polymerase I to prevent side reactions; adding dA-tail), followed by cooling down to 4° C. and keeping the temperature. The reaction product was taken out and inserted in ice or stored at −20° C. overnight.

Ligation: 1 μL of Ad153-2B adaptor (10 μM) was added.

The adaptor was formed through renaturation from two primers, i.e., set forth as SEQ ID NO:1 and SEQ ID NO:2:

Adaptor Primer 1: AGTCGGATCGTAGC-CATGTCGTTCCTTAGGAAGACAA (SEQ ID NO:1, this primer is 5' end-phosphorylated)

Adaptor Primer 2: TGTGAGC-CAAGGAGTTGXXXXXTTGTCTTCCTAA-GACCGCTTGGCCTCCG ACTT (SEQ ID NO: 2, where XX) (XXXXXXX is a barcode sequence; each X refers to a designed base A, T, C or G; and the barcode sequence is used as a molecular tag for distinguishing different samples)

Then, the following system was added:

| | Volume |
|---|---|
| 10X T4 DNA ligase buffer | 3.0 μL |
| Nuclease-free water | 12.4 μL |
| 50% polyethylene glycol-8000 | 12.0 μL |
| T4 DNA ligase (600 U/μL) | 1.6 μL |
| Total | 29 μL |

Mixing well, standing at 23° C. for 60 minutes, cooling down to 4° C. and keeping the temperature.

Purification of the ligated product: 30 μL of nuclease-free water and 40 μL of DNA Clean Beads was added for purification; 48 μL of 1×TET was added for dissolving, and 45 μL thereof was pipetted and transferred to a new 8-tube strip. It should be careful that the magnetic beads could not be brought into the PCR system.

For PCR amplification, primers and PCR Mix were added.

| | Volume |
|---|---|
| 10 μM Ad153-Primer Mix | 4 μL |
| 1 U/μL UDG | 1 μL |
| 2x HiFi PCR Mix | 50 μL |
| Total | 55 μL |

PCR was performed according to the following conditions:

| Temperature | Time |
|---|---|
| 37° C. | 15 min |
| 98° C. | 1 min |

-continued

| Temperature | Time | |
|---|---|---|
| 98° C. | 15 s | |
| 56° C. | 20 s | 15 cycles |
| 72° C. | 1 min | |
| 72° C. | 5 min | |
| 16° C. | hold | |

Purification of the PCR product: 90 µL of DNA Clean Beads were added for purification, 27 µL of 1×TET was added for dissolving, and 25 µL was pipetted and transferred to a new PCR tube.

The quantification was performed using Qubit dsDNA HS Assay Kit, and the library concentration was greater than 5 ng/µL.

The sequencing results of the experimental groups and the comparative groups are listed in Table 1 below.

TABLE 1

| | Alignment results | |
|---|---|---|
| | rRNA proportion % | Ref-Seq mRNA mapping rate % |
| Control group 1 | 0.38% | 21.00% |
| Control group 2 | 0.48% | 29.69% |
| Experimental group 1 | 0.58% | 24.20% |
| Experimental group 2 | 0.79% | 32.16% |

In Table 1, the comparative group 1 and the comparative group 2 were two parallel experiments, and the experimental group 1 and the experimental group 2 were two parallel experiments. In Table 1, the rRNA proportion represents data waste; and the RefSeq-mRNA mapping rate of the transcriptome represents a ratio of valid data.

It can be seen from the results shown in Table 1 that the rRNA proportion and the RefSeq-mRNA mapping rate obtained by the method of the experimental groups are similar to or even slightly better than those obtained by the conventional solution in the comparative groups. Therefore, the experimental groups of the present disclosure can obtain excellent detection results by adopting a simplified process.

Of course, because intron sequences can be captured in the schemes of the above experimental groups and comparative groups and these sequences cannot be mapped to RefSeq-mRNA, the obtained RefSeq-mRNA mapping rate is lower than that obtained by the oligo (dT) library construction method.

The strain splitting results of the experimental groups and the comparative groups are shown in Table 2 below:

TABLE 2

| | Strain splitting results | |
|---|---|---|
| | Mapped to opposite strand | Mapped to corresponding strand |
| Control group 1 | 3.85% | 96.15% |
| Control group 2 | 4.46% | 95.54% |

TABLE 2-continued

| | Strain splitting results | |
|---|---|---|
| | Mapped to opposite strand | Mapped to corresponding strand |
| Experimental group 1 | 3.76% | 96.24% |
| Experimental group 2 | 4.43% | 95.57% |

In Table 2, "mapped to opposite strand" means that the mRNA template strand is incorrectly determined, and "mapped to corresponding strand" means the correct determination of the mRNA template strand.

From the results provided in Table 2, it can be seen that the method provided by the present disclosure performs strain splitting similar to the conventional solution, indicating that the scheme is compatible with the dUTP-UDG strain splitting strategy.

FIG. 2 is the capillary electrophoresis diagram (detected by bioanalyzer 2100) of the PCR products, and FIG. 3 illustrates the insert size of RNA-Seq.

It can be seen from the results in FIG. 2 and FIG. 3 that the solution of the present disclosure and the comparative solution are also consistent in terms of the insert size.

In summary, the method for constructing a library based on an RNA sample and the method for sequencing provided by the present disclosure can perfectly substitute the existing schemes while reducing costs and shortening time.

In the description of the present disclosure, the terms "first", "second", etc. are only used for descriptive purposes, and cannot be understood as indicating or implying relative importance or implicitly indicating the number of indicated technical features. Therefore, the features defined with "first" and "second" may explicitly or implicitly include at least one of the features. In the description of the present disclosure, "plurality" means at least two, e.g., two, three, etc., unless otherwise specifically defined.

In the specification, descriptions with reference to the terms "one embodiment", "some embodiments", "examples", "specific examples", or "some examples" etc. mean that specific features, structure, materials or characteristics described in conjunction with the embodiment or example are included in at least one embodiment or example of the present disclosure. In the specification, the schematic representations of the above-mentioned terms are unnecessarily directed to the same embodiment or example. Moreover, the described specific features, structures, materials or characteristics can be combined in any one or more embodiments or examples in a suitable manner. In addition, those skilled in the art can combine and integrate the different embodiments or examples and the features of the different embodiments or examples described in the specification without contradicting each other.

Although the embodiments of the present disclosure have been illustrated and described above, it can be understood that the above-mentioned embodiments are exemplary and should not be construed as limiting the present disclosure. Those skilled in the art can make changes, modifications, substitutions, and variations to the above-mentioned embodiments within the scope of the present disclosure.

What is claimed is:

1. A method for constructing a library based on an RNA sample, the method comprising:

step 1 of subjecting the RNA sample to a reverse transcription reaction to obtain DNA-RNA hybrid strands;

step 2 of performing reaction of the DNA-RNA hybrid strands with an endoribonuclease, a first DNA polymerase, a second DNA polymerase, and dATPs to obtain a double-stranded DNA added with dA-tailing, wherein the first DNA polymerase has a 5'-3' exonuclease activity and a 3'-5' exonuclease activity, and the second DNA polymerase has no 3'-5' exonuclease activity;

step 3 of ligating the double-stranded DNA added with dA-tail and a sequencing adaptor to obtain a ligated product; and step 4 of subjecting the ligated product to PCR amplification to obtain a sequencing library.

2. The method according to claim 1, wherein the endoribonuclease is RNase H.

3. The method according to claim 1, wherein the first DNA polymerase is DNA polymerase I; and the second DNA polymerase is selected from the group consisting of Taq DNA polymerase, Tth DNA polymerase, Bst DNA polymerase, Bst DNA polymerase of larger fragment, Klenow Fragment (exo-), and combinations thereof.

4. The method according to claim 1, wherein the reaction in step 2 comprises: reacting at 10° C. to 20° C. for at least 1 hour and then reacting at 70° C. to 80° C. for 10 to 30 minutes to obtain the double-stranded DNA added with A-tailing.

5. The method according to claim 1, wherein a buffer used in the reaction in step 2 comprises magnesium ions at a final concentration ranging from 5 mM to 40 mM, Tris-Cl having a pH value between 6.5 and 8.5, and sodium or potassium ions at a final concentration of less than 100 mM.

6. The method according to claim 1, wherein step 1 further comprises:

step 1-1 of mixing and treating the RNA sample with 5' end-phosphorylated random primers at 80° C. to 95° C. for 5 minutes to 15 minutes to obtain a fragmented RNA product; and step 1-2 of mixing the fragmented RNA product with dNTPs, actinomycin D, an RNase inhibitor, and a reverse transcriptase for the reverse transcription reaction to obtain a first strand cDNA product.

7. The method according to claim 6, wherein the reverse transcription reaction comprises 10 minutes to 15 minutes at 25° C. to 30° C., 10 minutes to 20 minutes at 45° C. to 55° C., and 10 minutes to 20 minutes at 70° C. to 75° C.

8. The method according to claim 6, wherein the random primers have a length of 6 to 8 random nucleotides.

9. The method according to claim 1, further comprising, prior to step 4: purifying the ligated product using magnetic beads.

10. The method according to claim 1, wherein the RNA sample is a total RNA sample, an oligo (dT)-enriched mRNA sample, or an rRNA-free RNA sample.

11. A sequencing library, the sequencing library being constructed with the method according to claim 1.

12. A method for sequencing an RNA sample, comprising:

constructing a sequencing library based on an RNA sample with the method according to claim 1; and sequencing the sequencing library to obtain sequencing information of the RNA sample.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: adaptor primer1
<220> FEATURE:
<221> NAME/KEY: misc_feature
<222> LOCATION: (1)..(1)
<223> OTHER INFORMATION: Phosphorylated

<400> SEQUENCE: 1
agtcggatcg tagccatgtc gttccttagg aagacaa                            37

<210> SEQ ID NO 2
<211> LENGTH: 59
<212> TYPE: DNA
<213> ORGANISM: Artificial Sequence
<220> FEATURE:
<223> OTHER INFORMATION: Adaptor primer2
<220> FEATURE:
<221> NAME/KEY: misc_feature
<222> LOCATION: (18)..(27)
<223> OTHER INFORMATION: n is a, t,c, or g

<400> SEQUENCE: 2
tgtgagccaa ggagttgnnn nnnnnnnttg tcttcctaag accgcttggc ctccgactt       59
```